(12) United States Patent
Seal et al.

(10) Patent No.: US 11,517,531 B2
(45) Date of Patent: Dec. 6, 2022

(54) CERIUM OXIDE NANOPARTICLE COMPOSITIONS AND METHODS

(71) Applicant: University of Central Florida Research Foundation Inc., Orlando, FL (US)

(72) Inventors: Sudipta Seal, Oviedo, FL (US); Swetha Barkam, Orlando, FL (US); Amitava Adhikary, Rochester, MI (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 85 days.

(21) Appl. No.: 15/956,468

(22) Filed: Apr. 18, 2018

(65) Prior Publication Data
US 2018/0339913 A1 Nov. 29, 2018

Related U.S. Application Data

(60) Provisional application No. 62/486,612, filed on Apr. 18, 2017.

(51) Int. Cl.
| | |
|---|---|
| *A61K 9/51* | (2006.01) |
| *A61K 9/14* | (2006.01) |
| *C01F 17/235* | (2020.01) |
| *A61K 33/244* | (2019.01) |
| *B82Y 30/00* | (2011.01) |
| *B82Y 40/00* | (2011.01) |
| *B82Y 5/00* | (2011.01) |

(52) U.S. Cl.
CPC .................. *A61K 9/14* (2013.01); *A61K 9/51* (2013.01); *A61K 33/244* (2019.01); *C01F 17/235* (2020.01); *A61K 9/5115* (2013.01); *A61K 9/5192* (2013.01); *B82Y 5/00* (2013.01); *B82Y 30/00* (2013.01); *B82Y 40/00* (2013.01); *C01P 2002/01* (2013.01); *C01P 2002/84* (2013.01); *C01P 2002/85* (2013.01); *C01P 2002/86* (2013.01); *C01P 2004/62* (2013.01); *C01P 2004/64* (2013.01)

(58) Field of Classification Search
CPC .......... A61K 9/14; A61K 9/141; A61K 9/143; A61K 9/145; A61K 9/148; A61K 9/16; A61K 9/51; A61K 9/5107; A61K 9/5115; A61K 9/513
See application file for complete search history.

(56) References Cited

U.S. PATENT DOCUMENTS

2012/0103909 A1* 5/2012 Burba ...................... C02F 1/72
210/665

OTHER PUBLICATIONS

Heckert et al. (The role of cerium redox state in the SOD mimetic activity of nanoceria; Biomaterials, 29 (2008) 2705-2709 (Year: 2008).*
Heckler et al. (The role of cerium oxide redox state in the SOD mimetic activity of nanoceria; Biomaterials, 29 (2008) 2705-2709 (Year: 2008).*
Goharshadi et al (Fabrication of cerium oxide nanoparticles: Characterization and optical properties, Journal of Colloid and Interface Sciences 356, 473-480, 2011) (Year: 2011).*
Naganuma (The effect of cerium valence states at cerium oxide nanoparticle surfaces on cell proliferation, Biomaterials 35, 4441-4453, 2014) (Year: 2014).*
Renu et al. (Development of Cerium Oxide Nanoparticles and Its Cytotoxity in Prostate Cancer Cells; Advanced Science Letter; vol. 5, 1-9, 2012) (Year: 2012).*
Estes et al. (Tetravalent Ce in Nitrate-Decorated Hexanuclear Cluster [Ce6($\mu$3-O)4($\mu$3-OH)4]12+: A Structural End Point for Ceria Nanoparticles; The Journal of Physical Chemistry, 120, 5810-5818, 2016 (Year: 2016).*
Adhikary, A., et al, "The guanine cation radical: investigation of deprotonation states by ESR and DFT", J Phys Chem B, vol. 110, Issue 47, pp. 24171-24180 (2006).
Barkam, S., et al, "The change in antioxidant properties of dextran-coated redox active nanoparticles due to synergetic photoreduction-oxidation", Chem Eur J, vol. 21, pp. 12646-12656 (2015).
Celardo, I., et al., "Ce3+ Ions determine redox-dependent anti-apoptotic effect of cerium oxide nanoparticles", Am Chem Society, vol. 5, Issue 6, pp. 4537-4549 (2011).
Chigurupati, S., et al, "Effects of Cerium Oxide Nanoparticles on the growth of keratinocytes, fibroblasts and vascular endothelial cells in cutaneous wound healing", Biomaterials, vol. 34, Issue 9, pp. 2194-2201 (2013).
Das, S., et al, "The induction of angiogenesis by cerium oxide nanoparticles through the modulation of oxygen in intracellular enviornments", Biomaterials, vol. 33, Issue 21, pp. 7746-7755 (2012).

(Continued)

*Primary Examiner* — Micah Paul Young
(74) *Attorney, Agent, or Firm* — Timothy H. Van Dyke; Wolter, Van Dyke, Davis, PLLC

(57) ABSTRACT

Cerium oxide nanoparticles (CNPs) have been proven to exhibit antioxidant properties attributed to its surface oxidation states (Ce4+ to Ce3+ and vice versa) mediated at the oxygen vacancies on the surface of CNPs. Different anions in precursor cerium salts were used to prepare CNPs resulting in disclosed CNPs with varying physicochemical properties such as dispersion stability, hydrodynamic size, and the signature surface chemistry. The antioxidant catalytic activity and oxidation potentials of different CNPs have been significantly altered with the change of anions in the precursor salts. For one, CNPs prepared using precursor salts containing $NO_3^-$ and $Cl^-$ ions exhibited increased antioxidant activity than previously thought possible. The change in oxidation potentials of CNPs with the change in concentration of the nitrate and chloride ions indicates the disclosed CNP's have different surface chemistry and antioxidant properties. These compositions and methods of their synthesis are disclosed.

5 Claims, 6 Drawing Sheets

(56) References Cited

OTHER PUBLICATIONS

Das, S., et al, "Cerium oxide nanoparticles: applications and prospects in nanomedicine", Nanomedicine, vol. 8, Issue 9, pp. 1483-1508 (2013).

Deshpande, S., "Size dependency variation in lattice parameter and valency states in nanocrystalline cerium oxide", Applied physics letters, vol. 87, 3 pages (2005).

Dowding, J., et al, "Cellular interaction and toxicity depends on physiochemical properties and surface modification of redox active nanomaterials", ACS Nano, vol. 7, Issue 6, pp. 4855-4868 (2013).

Eguchi, et al, "Electrical properties of ceria-based oxides and their application to solid oxide fuel cells", Solid State Ionics, vol. 52, pp. 165-172 (1992).

Freitas C. & Muller R., "Effect of light and temperature on zeta potential and physical stability in solid lipid nanoparticle (SLN) dispersions", International J of Pharmeutics, vol. 168, pp. 221-229 (1998).

Gu H. & Soucek M., "Preparation and characterization of monodispersecerium oxide nanoparticles in hydrocarbon solvents", Chem. Mater., vol. 19, pp. 1103-1110 (2007).

He Y., "Synthesis of polyaniline/nano-CeO2 composite microspheres via a solid-stabilized emulsion route", Mater. Chem. Physics, vol. 92, pp. 134-137 (2005).

Heckert E, et al., "The role of cerium redox state in the SOD mimetic activity of nanoceria", Biomaterials, vol. 29, Issue 18, pp. 2705-2709 (2008).

Hirano M, & Kato E., "Hydrothermal synthesis of cerium(IV) oxide", J Am Ceram Soc, vol. 79, Issue 3, pp. 777-780 (1996).

Hirano M., et al., "Preparation and spherical agglomeration of crystalline cerium(IV) oxide nanoparticles by thermal hydrolysis", J Am Ceram Soc, vol. 85, Issue 5, pp. 1287-1289 (2000).

Hirst S., et al, "Anti-inflammatory properties of cerium oxide in nanoparticles", Small J, vol. 5, Issue 24, pp. 2848-2856 (2009).

Karakoti AS, et al., "Nanoceria as antioxidant: synthesis and biomedical applications", JOM, vol. 60, Issue 3, pp. 33-37 (2008).

Karakoti AS, et al, "Preparation and characterization challenges to understanding environmental and biological impacts of nanoparticles", Surf Interface Anal, vol. 44, Issue 5, pp. 882-889 (2012).

Korsvik C, et al, "Superoxide dismutase mimetic properties exhibited by vacancy engineered ceria nanoparticles", Chem Commun, pp. 1056-1058 (2007).

Kumar A., et al, "Luminescence Properties of Europium-doped cerium oxide nanoparticles: role of vacancy and oxidation states", Langmuir, vol. 25, Issue 18, pp. 10998-11007 (2009).

Langergraber G., et al., "A Multivariate calibration procedure for UV/VIS spectrometric quantification of organic matter and nitrate in wastewater", AutMoNet, pp. 25-32 (2002).

Lohse S, & Murphy J., "Applications of colloidal inorganic nanoparticles: from medicine to energy", J Am Chem Soc, vol. 134, pp. 15607-15620 (2012).

Lynch I, & Dawson K., "Protein-nanoparticle interactions", NanoToday, vol. 3, pp. 40-47 (2008).

Masui T, et al., "Synthesis of BN-coated CeO2 fine powder as a new UV blocking material", J Mater Chem, vol. 10, pp. 353-357 (2000).

Masui T., et al., "Synthesis of cerium oxide nanoparticles by hydrothermal crystallization with citric acid", J Mater Science Lett, vol. 21, pp. 489-491 (2002).

Patil S, et al., "Protein adsorption and cellular uptake of cerium oxide nanoparticles as a function of zeta potential", Biomaterials, vol. 28, Issue 31, pp. 4600-4607 (2007).

Pirmohamed T, et al., "Nanoceria exhibit redox state-dependent catalase mimetic activity", Chem Commun (camb.), vol. 46, Issue 16, pp. 2736-2738 (2010).

Rodriguez J, et al, "Water-gas shift reaction on a highly active inverse CeOx/Cu(111) catalyst: unique role of ceria nanoparticles", Agnew. Chem. Int. Ed., vol. 48, pp. 8047-8050 (2009).

Schubert D., et al, "Cerium and yttrium oxide nanoparticles are neuroprotective", Biochem. Biophys. Res. Commun., vol. 342, pp. 86-91 (2006).

Sun C, et al., "Nanostructured ceria-based materials: synthesis, properties, and applications", Energy Environ. Sci., vol. 5, pp. 8475-8505 (2012).

Wang D., et al, "Synthesis and oxygen storage capacity of two-dimensional ceria nanocrystals", Agnew. Chem. Int. Ed., vol. 50, pp. 4378-4381 (2011).

Xu J., et al., "size dependent oxygen buffering capacity of ceria nanocrystals", Chem. Commun., vol. 46, pp. 1887-1889 (2010).

Yang J., et al, "Study of polishing characteristics of monodisperse ceria abrasive in chemical mechanical planarization", J Electrochemical Society, vol. 157, Issue 3, pp. H235-H240 (2010).

Yin L, et al., "Sonochemical synthesis of cerium oxide nanoparticles—effect of additives and quantum size effect" J Colloid Interface Science, vol. 246, pp. 78-84 (2002).

Zhang F., et al., "Ceria nanoparticles: size, size distribution, and shape", J. Applied Physics, vol. 95, Issue 8, pp. 4319-4326 (2004).

Barkam S., et al, "Modulating the catalytic activity of cerium oxide nanoparticles with the anion of the precursor salt", J Phys Chem, vol. 121, pp. 20039-20050 (2017).

\* cited by examiner

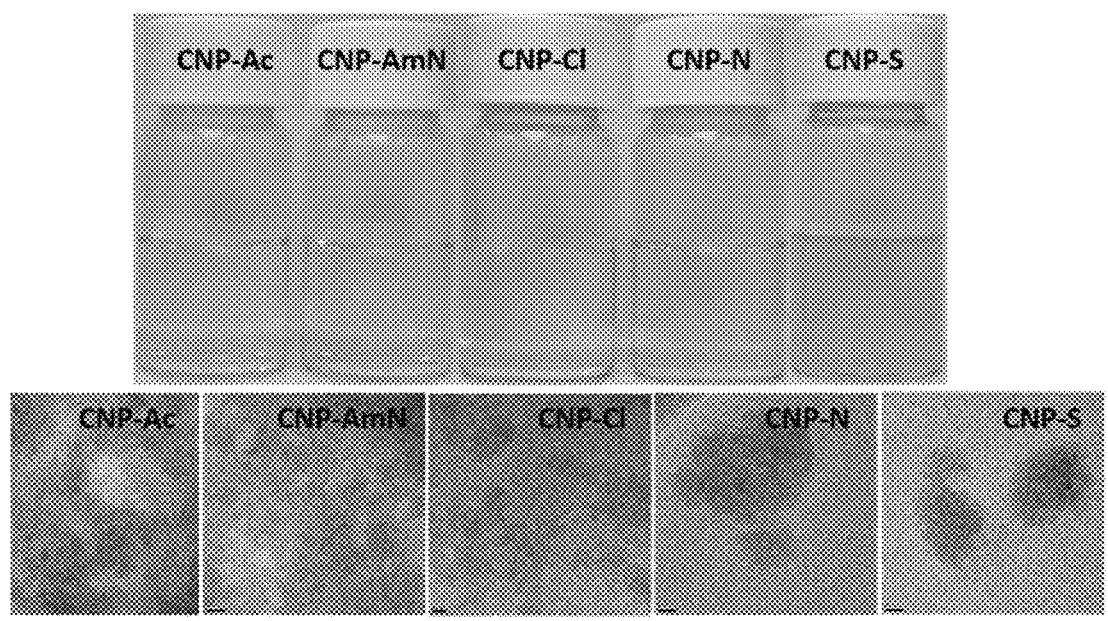
FIG. 1A
FIG. 1B
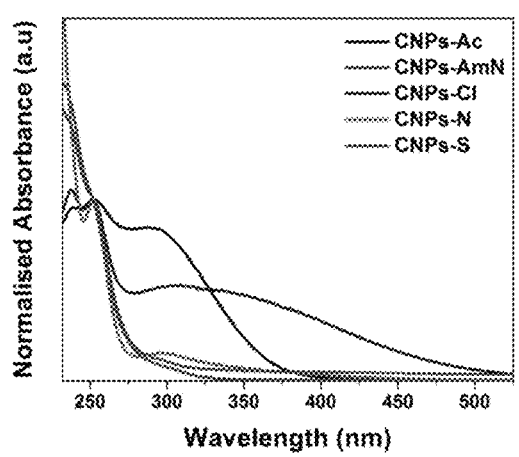
FIG. 2A
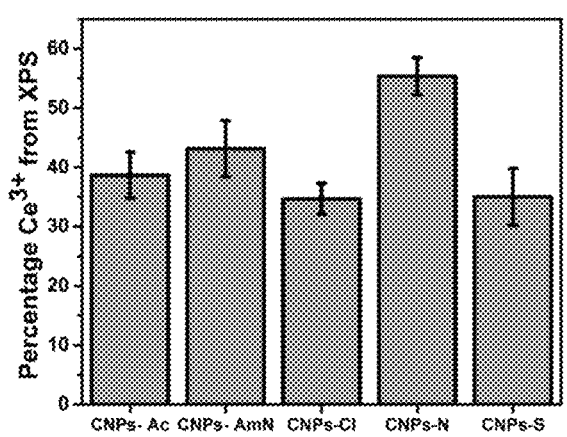
FIG. 2B

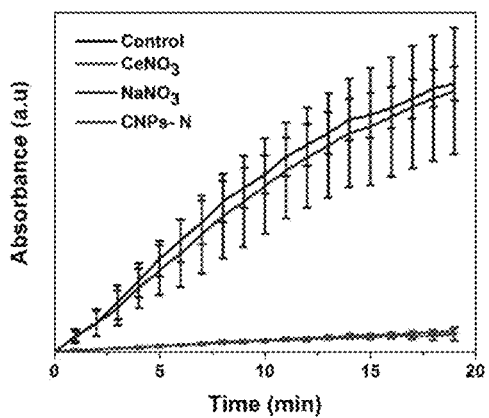
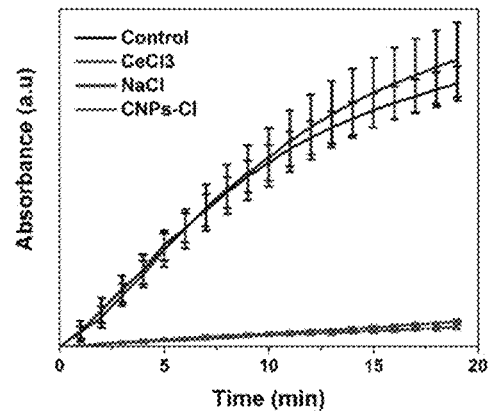
FIG. 5A  FIG. 5B
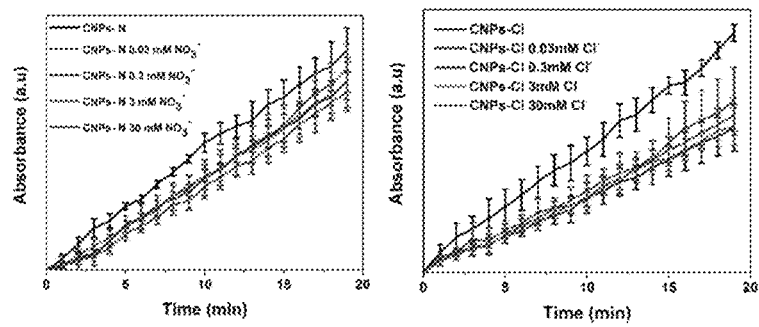
FIG. 6A  FIG. 6B
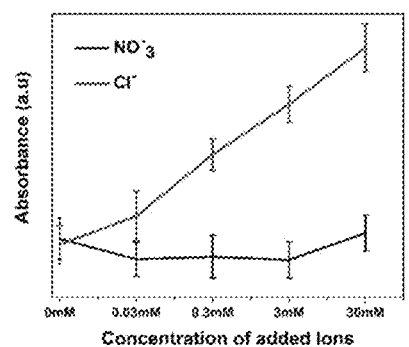
FIG. 6C

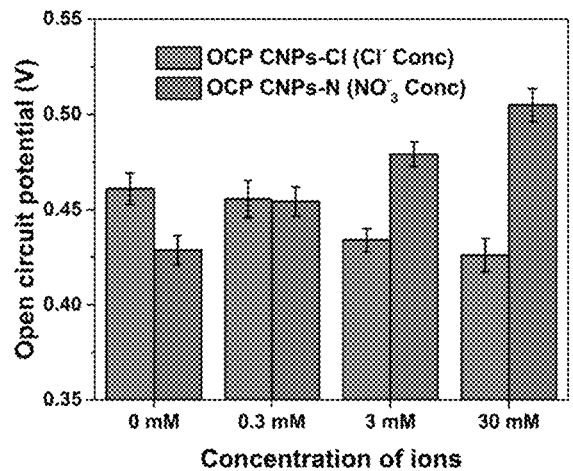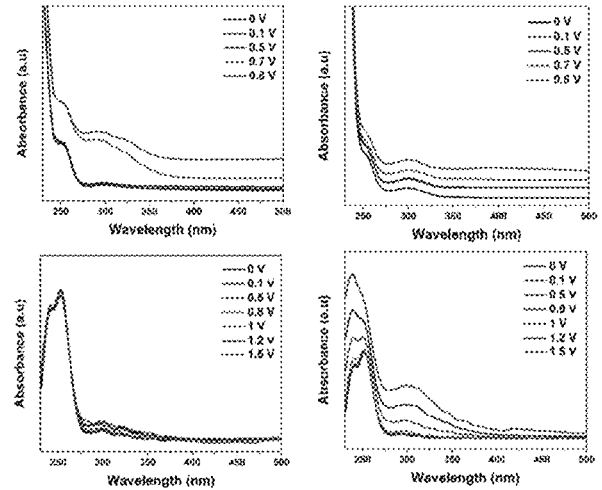
FIG. 7A  FIG. 7B  FIG. 7C  FIG. 7D  FIG. 7E
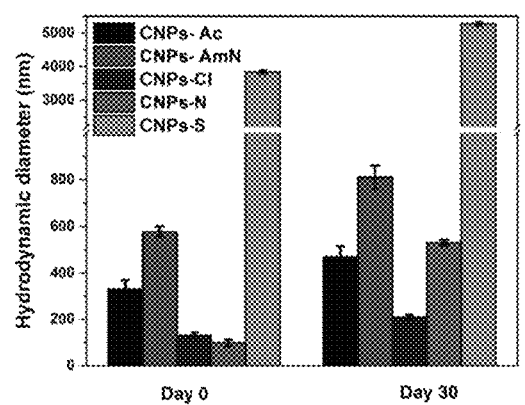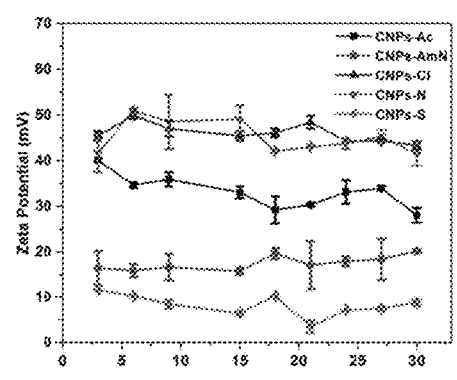
FIG. 8A  FIG. 8B

CERIUM OXIDE NANOPARTICLE COMPOSITIONS AND METHODS

GOVERNMENT SUPPORT

This invention was made with Government support under agency contract/grant nos. CA045424 awarded by the National Institutes of Health. The Government has certain rights in this invention.

BACKGROUND

Nanoparticles have been changing the facade to nanotechnology with their advanced characteristics features and properties attributed to miniature size and morphology. The properties of nanoparticles due to their small size have generated a plethora of applications in the field of biomedicine, optics, energy science etc. [1]. Ceria nanoparticles (CNPs) have proven to be novel material in the field of nanomedicine and have potential application in drug delivery systems with therapeutic abilities. The revelation of CNPs having antioxidant mimetic properties has led to exploration as a possible therapeutic for pathologies related to oxidative stress [2]. Previously, ceria has been known for its application in catalysis, electrolyte in solid oxide fuel cells, chemical mechanical polishing, ultraviolet shielding etc. [3-6]. The nano size property of CNPs has enabled them to replicate naturally existing enzymes such as superoxide dismutase (SOD), catalase etc. by scavenging and modulating the reactive oxygen species (ROS) concentration in the microenvironment around the nanoparticles [7]. CNPs can be delicately formulated for both the oxidation states of cerium, $Ce^{4+}$ and $Ce^{3+}$, to coexist on the surface of CNPs. The regenerative property of CNPs is the result of switching of oxidation states from $Ce^{3+}$ to $Ce^{4+}$ and vice versa which enables them to perform as antioxidants [8]. This simultaneous coexistence of both the oxidation states in different ratios creates oxygen vacancies, which increases with decrease in size and plays a crucial role in tunneling the surface chemistry of CNPs. These oxygen vacancies act as potential hotspots for pronounced catalytic activity, and is ultimately responsible for the CNPs' antioxidant properties [9]. Therefore, CNPs are found to be effective against pathologies associated with chronic oxidative stress (such as cancer, neurodegenerative diseases, etc.) and inflammation [10]. They are well tolerated in both in vitro and in vivo biological models, which makes CNPs suitable for nanobiology and regenerative medicine applications [2]. For example, inducement of angiogenesis by CNPs with a high [Ce3+]:[Ce4+] ratio aids in wound healing by promoting cell growth/tissue engineering through antioxidant activity [11].

There are several synthesis methods that have been adopted for preparing cerium oxide nanomaterials for different applications such as hydrothermal, spray pyrolysis, thermos hydrolysis, electrochemical synthesis, wet chemical, gas condensation, microemulsion, solvothermal, solgel and sonochemical synthesis [7, 12, 13, and 14]. The interaction at the nano-bio interface can be significantly influenced by the physical properties of nanoparticles such as size, surface charge, agglomeration, and the coating of biomolecule/polymer on the surface. The chemical properties of CNPs such as the surface chemistry regulated by the surface [Ce3+]:[Ce4+] ratio can significantly modulate the bioactivity and antioxidant property of CNPs [12, 15, 16]. It has been previously reported that the physical properties of CNPs are influenced by the synthesis methods and parameters, generally speaking.

The presence of biomolecules or polymers or a chemical entity can alter the physical and chemical properties of CNPs. For instance, the presence of a polymer coating improves the dispersion stability and decreases the agglomeration of particles in biological media. The protein corona formation in the biologically relevant media is regulated by the dispersion stability and the presence of any chemical entity on CNPs, thereby deciding the cellular internalization of the nanoparticles [7, 17]. As another example, it has been illustrated that the high temperature synthesis methods of CNPs generally have higher particle size, size distribution and degree of agglomeration. On the other hand, room temperature synthesis techniques such as microemulsion and wet chemical provides better control of particle size distribution and generated lower particles size (<10 nm). Wet chemical synthesis provides the advantage of creating homogenous distribution of small sized (3-5 nm) particles with stable dispersion, which are perfectly suitable for biomedical applications [18]. The pH of the solution can be regulated to modulate its dispersion stability with increased suspension in acidic pH. The ratio of [Ce3+]:[Ce4+] is one of the crucial factors that determines the antioxidant property of CNPs, regulating their bioactivity. It is generally observed that in the ratio of surface [Ce3+]:[Ce4+] is higher in room temperature preparation using wet chemical synthesis.

It has been reported that the CNPs prepared using a base such as ammonium hydroxide or sodium hydroxide have high Ce4+ concentration on the surface ([Ce3+]:[Ce4+]~21-30%). Whereas the CNPs prepared in oxidizing atmosphere of $H_2O_2$ have high Ce3+ concentration on the surface of CNPs ([Ce3+]:[Ce4+]~55-65%)[13, 19-21]. The surface chemistry can be additionally modified by changing the pH of the dispersion and by doping CNPs. It is important to note that all of the above results involved use of cerium nitrate hexahydrate salt as the precursor salt to prepare CNPs with different oxidizing/reducing agents to create different physicochemical properties.

BRIEF DESCRIPTION OF THE DRAWINGS

FIG. 1A-B. FIG. 1A demonstrates the solutions of CNPs prepared using cerium acetate (CNPs-Ac), cerium ammonium nitrite (CNPs-AmN), cerium chloride (CNPs-Cl), cerium nitrate (CNPs-N), and cerium sulfate (CNPs-S) precursors. All of the CNPs solutions appear to be stable as there do not exhibit any turbidity or precipitation accept for CNPs-S which shows turbidity and precipitation indicating dispersion instability. FIG. 1B shows transmission electron microscopy images of CNPs-Ac, CNPs-AmN, CNPs-Cl, CNPs-N and CNP—S. The images depict the crystallinity of CNPs prepared from all different precursors.

FIG. 2A-B. FIG. 2A shows the UV-visible spectrophotometry of different CNPs have been recorded every 6 days for a duration of 30 days of their formation. In case of CNPs-Ac, CNPs-Cl and CNPs-N, the peak intensities of Ce3+ and Ce4+ are more prominent compared to that of CNPs-AmN and CNPs-S. CNPs-Cl sample depicted higher intensities of both Ce4+ and Ce3+ whereas CNPs-Ac and CNPs-N higher intensity of Ce3+ compared to that of Ce4+. in case of CNPs-Ac, CNPs-Cl and CNPs-N. FIG. 2B shows the XPS results indicate that the % Ce3+ on the surface of CNPs is higher in case of CNPs-N followed by CNPs-AmN. CNPs-Cl and CNPs-S have approximately the same amount of Ce3+ concentration on the surface of CNPs. Furthermore, CNPs-Ac has the least amount of Ce3+ on the surface of CNPs.

FIG. 3A shows the SOD mimetic activity of CNPs prepared using different precursors. FIG. 3(B) shows that % of antioxidant capacity of CNPs analyzed from SOD mimetic data also correlates with the above data.

FIG. 5A-B: SOD assay results. FIG. 5A shows the SOD assay of $CeNO_3$, which exhibits SOD mimetic activity due to the presence of Ce3+ ions in the system, $NaNO_3$ which does not exhibit SOD mimetic activity as $NO_3^-$ and Na+ ions by themselves are not SOD active and CNPs-N is SOD mimetic active as is known from previous results. FIG. 5B shows the SOD assay of $CeCl_3$, which exhibits SOD mimetic activity due to the presence of Ce3+ ions in the system, NaCl which does not exhibit SOD mimetic activity as Cl- and Na+ ions by themselves are not SOD active and CNPs-Cl is SOD mimetic active as is known from previous results.

FIG. 6A-C. FIG. 6A shows SOD mimetic activity of CNPs-N with various concentration of NO3- ion by the addition of $NaNO3$ at different concentrations of 0.03 mM, 0.3 mM, 3 mM and 30 mM. FIG. 6B shows SOD mimetic activity of CNPs-Cl with various concentration of Cl ion by the addition of NaCl at different concentrations of 0.03 mM, 0.3 mM, 3 mM and 30 mM. FIG. 6C is a graph depicting the SOD % antioxidant property of CNPs-N with increasing concertation of NO3- ion concentration and of CNPs-Cl with increasing concentration of Cl- ion concentration. There is a clear change in SOD mimetic activity of CNP-Cl with increasing concentration of Cl ion compared to that of NO3- ion.

FIG. 7A-E: UV-Visible spectro-electrochemical results. FIG. 7A shows open circuit potentials (OCP) values are presented of CNPs-Cl with changing concentrations of Cl- (0, 0.3 mM, 3 mM and 30 mM) and of CNPs-N with changing concentrations of NO-3 ions. It can be clearly observed that the OCP of CNPs-N increases with increase in concentration of NO-3 ions whereas the OCP of CNPs-Cl decreases with increase in concentration of Cl-. FIG. 7B shows a UV-Visible graph of Ce3+ peak of CNPs-N after applying varying voltages of 0V, 0.1V, 0.5V, 0.7V, 0.8V, depicting increase in the intensity of Ce3+ peak with increase in voltage. This indicates that there was an oxidation of Ce3+ with the increase in voltage of the CNPs-N peak. FIG. 7C shows a UV-Visible graph of Ce3+ peak of CNPs-N with the addition of 30 mM NO-3 ions after applying varying voltages of 0V, 0.1V, 0.5V, 0.7V, 0.8V, depicting a decrease in intensity of increase of Ce3+ peak. This indicates that there is an oxidation of Ce3+ with the increase in voltage of the CNPs-N peak with decreased intensity. FIG. 7D shows a UV-Visible graph of Ce3+ peak of CNPs-Cl after applying varying voltages of 0V, 0.1V, 0.5V, 0.8V, 1V, 1.2V, 1.5V depicting no change in the intensity of Ce3+ peak with increase in voltage. This indicates that there was no oxidation of Ce3+ with the increase in voltage in CNPs-Cl. FIG. 7E shows a UV-Visible graph of Ce3+ peak of CNPs-Cl with the addition of 30 mM Cl- ions after applying varying voltages of 0V, 0.1V, 0.5V, 0.8V, 1V, 1.2V, 1.5V depicting an increase in the intensity. This indicates that there is an oxidation of Ce3+ with the increase in voltage of the CNPs-Cl in presence of additional Cl- ions.

FIG. 8A-B. FIG. 8A shows the size and the zeta potential of the nanoparticles have been investigated over a period of 30 days to observe the dispersion stability of the nanoparticles using dynamic light scattering (DLS). FIG. 8B depicts the change in size and zeta potential of CNPs-Ac, CNPs-AmN, CNPs-Cl, CNPs-N and CNPs-S. It can be clearly observed that the hydrodynamic diameter of nanoparticles on day 0 started of smaller compared to their increased diameter with time on day 30. The zeta potential analysis indicates that the dispersion increases in the order of CNPs-S<CNPs-AmN<CNPs-Ac<CNPs-Cl≈CNPs-N. The low hydrodynamic size and high zeta potential are indication of stable particles which depicts higher catalytic activity due to higher surface area and increased stability.

FIG. 9A shows ESR spectrum (blue) obtained after UV-photoionization at 254 nm (2 min, 77 K) of 5'-dGMP (2 mg/mL) in 7.5 M LiCl/H2O and in the presence of 2.5 mM CNPs-N. Spectrum (pink) obtained after 77 K γ-irradiation (absorbed dose=500 Gy) of NaNO3 (1 mg/mL) in 7 M LiBr/D2O. Green spectrum is the simulated spectrum (for simulation parameters, see text). FIG. 9B shows ESR spectrum (black) obtained after UV-photoionization at 254 nm (2 min, 77 K) of 5'-dGMP (2 mg/mL) in 7.5 M LiCl/H2O in the presence of 2.5 mM CNPs-Cl. Spectrum (red) was obtained after annealing the sample of 5'-dGMP in 7.5 M LiCl at 150 K for 10 min. This sample was originally γ-irradiated (77 K, absorbed dose=2.5 KGy). All experimental spectra (blue, pink, black, red) were recorded at 77 K.

DETAILED DESCRIPTION

Figure 3A:
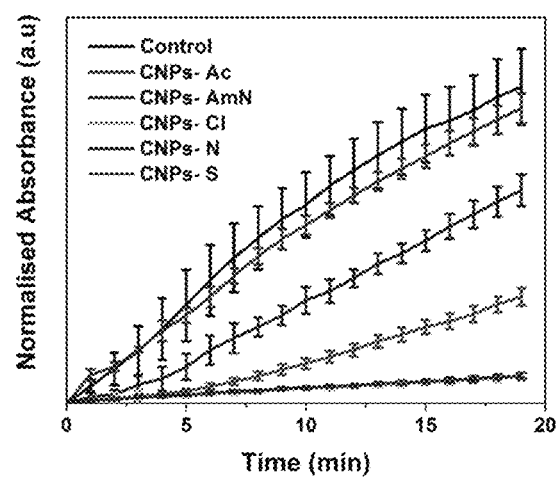
FIG. 3A-B.

Embodiments described herein are based on the discovery that varying the cerium precursor salt in the production of CNPs results in CNPs with different properties. One unexpected discovery is a composition (disclosed and described below) comprising CNPs having a predominant 4+ surface charge, but which also exhibits significant SOD mimetic activity. This CNP was synthesized using a precursor salt containing the chloride anion and is disclosed and characterized below. The present inventors have discovered these CNPs exhibit higher than usual SOD mimetic activity, given what was previously known about charge dominance on the surface of the CNPs and their respective catalytic activity. Namely, CNP's with higher Ce4+ on the surface are not known to exhibit high SOD mimetic activity, favoring catalase mimetic activity instead.

The term "predominant 4+ surface charge" refers to the concentration of cerium ions on the surface and means that the [Ce3+]:[Ce4+] ratio on the surface of the cerium oxide nanoparticle is less than 50%. In a specific example, cerium oxide nanoparticles having a predominant 4+ surface charge have a [Ce3+]:[Ce4+] ratio that is 40% or less.

The term "predominant 3+ surface charge" means that the [Ce3+]:[Ce4+] ratio on the surface of the cerium oxide nanoparticle is greater than 50%. In a specific example, the [Ce3+]:[Ce4+] ratio is greater than 60%.

The term "wet chemical synthesis" refers to a method of making CNPs that involves dissolving a cerium precursor salt in water followed by addition of hydrogen peroxide. In a specific example, the CNPs are stabilized over a predetermined time period, typically at least 15-30 days.

This disclosed composition includes not only the CNPs themselves (formed by using any precursor), but may further include the addition of chloride ions in the presence of the CNPs. These chloride ions may be in solution surrounding the CNPs at various concentration levels. In one embodiment, the concentration of the chloride ions in the presence of the CNPs is at least 0.03 mM. In yet another embodiment, a method for synthesizing a cerium nanoparticle composition comprising reducing a cerium precursor salt having a chloride anion or nitrate anion to form cerium nanoparticles (CNPs). This method may further include placing the CNPs in the presence of the chloride anion, which results in greater SOD mimetic activity than previously thought possible.

The following examples are provided as an aid in examining particular aspects of the invention, and represent only certain embodiments and explanations of embodiments. The examples are in no way meant to be limiting of the invention scope. The materials and methods provided below are those which were used in performing the examples that follow.

Other embodiments disclosed include methods for preparing CNPs using certain precursor salts (referred to herein as "Salts" or "precursor"), as well as the resulting compositions (CNPs). The disclosed CNPs have different physicochemical properties not yet reported to the best of the present inventors' knowledge. The extensive physiochemical and bioactive properties of CNPs synthesized using wet chemical synthesis in oxidizing environment created by $H_2O_2$ using these salts is disclosed. Apart from the physical properties, the surface chemistry and the change in antioxidant properties of different CNPs synthesized using the different cerium salt as demonstrated in the examples below is disclosed. The chemistry of the anion (from the salt) in relation to the surface chemistry of the disclosed CNPs and their antioxidant properties have been additionally verified by in-situ UV-Visible spectro-electrochemical analysis.

Radiation Protection and Dosing

The studies described in the Examples below show that certain CNPs (e.g. CNP-Cl) show remarkable ability to scavenge radiation-generated electrons. An effective amount or a therapeutically effective amount as used herein means the amount of the composition that, when administered to a subject for treating radiation exposure is sufficient to alert a treatment (as defined above). The therapeutically effective amount will vary depending on the formation of the composition, formulation or combination, the severity and timing of exposure to radiation and the age, weight, physical condition and responsiveness of the subject to be treated. Subjects include mammals, such as humans, mice, rats, dogs, cats, cows, pigs and non-mammals such as chickens, turkeys or other animals.

The compositions described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or transmucosal. In the Examples, the CNP were provided via intraperitoneal injection. Thus the compositions may be formulated as an ingestable, injectable, or topical formulation or for delivery via an osmotic pump. The compositions could also be provided as an aerosol formulation for direct delivery to the lung via inhalation. The compositions may also be delivered within a liposomal or time-release vehicle. Administration of the compositions to a subject in accordance with the invention appears to exhibit beneficial effects in a dose-dependent manner. Thus, within broad limits, administration of larger quantities of the compounds is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the compositions being administered, the formulation of the composition, the disease to be treated or inhibited, the condition of the subject, and other relevant medical factors that may modify the activity of the composition or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages liar a given patient can be determined using conventional considerations, e.g., by customary comparison of the differential activities of the compositions and of a known agent, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the composition will reduce morbidity and/or mortality by at least 10%, 20%, 30%, 40%, 50%. 60%, 70%, 80%, 90% or 100% compared to morbidity or mortality if the radiation exposure is left untreated. It is specifically contemplated that pharmaceutical preparations and compositions may palliate or alleviate symptoms of radiation exposure without providing a cure, or, in some embodiments, may be used to reverse the effects of radiation exposure.

The cerium oxide nanoparticles may be administered at a dosage between about 0.00005 mg/kg and 0.5 mg/kg. Suitably, the dosage is between about 0.005 mg/kg and 0.05 mg/kg. In the examples, the dosages used were between about 0.00007 mg/kg and 0.007 mg/kg. The composition may be formulated such that the cerium oxide nanoparticles are between 10 nM and 10 µM. Suitably, the cerium oxide nanoparticles are present at between 100 nM and 1 µM in the composition.

The compositions may be administered as a single dose or as multiple doses. Suitable effective total dosage amounts for administering the compositions may be determined by those of skill in the art, but typically range from about 50 nanograms to about 1 milligram per kilogram of body weight, although they are typically about 1-100 micrograms per kilogram of body weight. The dosage used in the Examples and shown to be effective was about 56 µg/kg given in 8 doses of 7 µg/kg in each dose. Large doses may be required for therapeutic effect and toxicity of the composition is low. In some embodiments, the effective dosage amount ranges from about 1 to about 100 micrograms per kilogram of body weight weekly. In another embodiment, the effective dosage amount ranges from about 5 to about 5,000 micrograms per kilogram of body weight over the course of treatment. Notably the dose of 7 µg/kg in 8 total doses used in the Examples was effective to offer substantial protection against a lethal radiation dose when administration began after radiation exposure. Those of skill in the art will appreciate that lower doses may be effective if the radiation exposure is sub-lethal or if the compositions described herein are provided in advance of radiation exposure as a radioprotective agent and not solely to mitigate previous radiation exposure. The effective dosage amounts described herein refer to total amounts administered, that is, if more than one dosage is administered in a period of time, the effective dosage amounts correspond to the total amount administered.

If the composition is administered as more than one dose or as divided doses, the dosage rate and amount may be modified accordingly. For example, the composition may be administered two or more times separated by 4 hours, 6 hours, 8 hours, 12 hours, a day, two days, three days, four days, one week, two weeks, or by three or more weeks, in the Examples, the compositions were given two times per week for a period of four weeks. The compositions may be provided for longer than four weeks, for example for two, three, four months or more.

The cerium oxide nanoparticles may be co-administered with other pharmaceuticals or compositions either in a unitary composition or as two separate compositions. Co-administration of cerium oxide nanoparticles with other compositions may be administered in any order, at the same time or as part of a unitary composition. The two may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

Examples. Synthesis and Characterization of CNPs from Different Cerium Salts

The Examples described below are also supported by Barkam et al. *J. Phys. Chem.* C 121, 36, 20039-20050, which is incorporated herein in its entirety. CNPs were prepared using wet chemical synthesis as described previously [22]. Five different CNPs were prepared using five different cerium salts, namely cerium acetate, cerium ammonium nitrate, cerium chloride, cerium nitrate and cerium sulfate. All of the CNPs were synthesized using the same method in which the cerium salt solutions were prepared by stirring the salt solutions for one hour to achieve a final concentration of 5 mM of CNPs. 30% $H_2O_2$ was added to the solutions to initiate oxidation of the cerium salts followed by thorough stirring to form crystalline CNPs. All the samples were allowed to stabilize in the dark for 30 days and then analyzed for physiochemical properties.

Characterization of CNPs

The hydrodynamic size and zeta potential were measured using Zeta Sizer Nano (Malvern Instruments). The Zeta sizer uses dynamic light scattering (DLS) technique which operates using a laser of 633 nm wavelength. High resolution transmission electron microscopy (HR-TEM) images were obtained using Philips (Tecnai Series) TEM operating at 300 KV. Lambda 750S UV/VIS spectrometer (Perkin Elmer) was used to obtain UV-visible spectra. A 10 mm path length quartz cuvette was used to perform the measurements. The surface chemistry illustrated by the concentration of $Ce^{3+}$ was calculated form the X-ray photoelectron spectroscopy (XPS) spectra of Ce 3d using a 5400 PHI ESCA (XPS) spectrometer. Mg-Kα X-ray radiation (1253.6 eV) was used at a power of 300 watts for taking the XPS measurements at a base pressure of 10-9 Torr. A reference peak of C-1s at 284.8 eV was used to compensate any peak shift due to charging effects.

Analysis of SOD Mimetic Activity

A superoxide dismutase assay kit was used to measure the SOD mimetic activity of all the CNPs. The kit uses a water-soluble tetrazolium reagent salt, WST-1 that converts into a formazan dye upon reduction due to presence of superoxide anion. FLUOstar Omega (BMG labtech) UV-Visible spectroscopy was used to measure the absorbance of WST-1 formazan dye at 440 nm in a 96 well plate. The kinetics of the reaction were recorded up to 30 min and analyzed for their % antioxidant SOD mimetic activity. 1 mM CNPs solutions were used to measure the SOD mimetic activity and pure water was used a control sample that does not have SOD mimetic activity.

In-Situ UV-Visible Spectro-Electrochemical Set Up

UV-visible spectro-electrochemical measurements were obtained to gauge the change in surface chemistry in the presence of different anions by oxidizing the solution by simultaneous application of voltage to the CNPs solution. A Lambda 750S UV/VIS spectrometer (Perkin Elmer) was used to perform the experiments in which the sample cuvette has an electrochemical cell set up. The cell set up had reference, counter and working electrodes that were placed inside the UV-Visible cuvette. The components of the cell were; Ag/AgCl electrode as reference electrode, thin platinum mesh of 1 cm×0.7 cm as working electrode and a thin platinum wire as counter electrode. The cuvette used in our experiments has a path length of 2 mm and autozero corrections are performed to eliminate the effects of all the electrodes inside the cuvette before running the experiments. The open circuit potentials were measured inside the cuvette by taking the measurements for 20 min until the value reaches an equilibrium. Chrono-amperometry was performed by applying a constant voltage for 3 min while UV-Visible spectrum was simultaneously recorded.

Synthesis and Characterization of CNPs Prepared Using Different Precursor

The present inventors prepared CNPs using different precursors having various counter anions. Examples of precursors and their associated anions include cerium acetate, cerium ammonium nitrite, cerium chloride, cerium nitrate and cerium sulfate. Samples may be prepared the same way using hydrogen peroxide to reduce the precursor salts to cerium oxide nanoparticles (CNPs). Additionally, a time based physiochemical characterization of the CNPs was carried out to observe the changes in size and zeta potential during the stabilization period of 30 days. This shall give a deep insight into the dispersion stability of the resulting CNPs which can help discern the catalytic properties for antioxidant properties.

FIGS. 1A-1B demonstrate the solutions of CNPs prepared using cerium acetate (CNPs-Ac), cerium ammonium nitrite (CNPs-AmN), cerium chloride (CNPs-Cl), cerium nitrate (CNPs-N), and cerium sulfate (CNPs-S). All of the CNPs solutions except CNPs-S appear to be stable as there do not exhibit any turbidity or precipitation. CNPs-S exhibit turbidity and precipitation indicating dispersion instability. Furthermore, initially on day 0 when the samples were prepared, the CNPs-Cl and CNPs-N solutions were transparent yellow in color which turned to transparent over the duration of 30 days. This has been previously observed in CNPs-N and has been concluded to arise from the addition of hydrogen peroxide to cerium salts to prepare CNPs.

The size and the zeta potential of the nanoparticles were investigated over a period of 30 days to observe the dispersion stability of the nanoparticles using dynamic light scattering (DLS). FIGS. 8A-8B depict the change in size and zeta potential of CNPs-Ac, CNPs-AmN, CNPs-Cl, CNPs-N and CNPs-S. It can be clearly observed that the hydrodynamic diameter of nanoparticles on day 0 started of smaller compared to their increased diameter with time on day 30. All of the nanoparticles, except that of CNPs-S which depicts turbidity, show smaller size due to dispersion stability. In case of CNPs-S, the DLS measurements might not give accurate results due to scattering phenomenon and the exposed volume of sample to the beam might not contain enough CNPs as they are precipitated due to unstable dispersion stability [23].

Similarly, the zeta potential of the nanoparticles shows a close relation to the hydrodynamic size data, which depicts that the CNPs-S has the least zeta potential which is almost constant with time. It has been established that zeta potentials of colloidal solutions of more than 30 mV are considered to be stable dispersion of nanoparticles[24]. CNPs-S depicts decreased zeta potential with highest hydrodynamic size indicating lowest dispersion stability followed by CNPs-AmN. This indicates that the dispersion increases in the order of CNPs-S<CNPs-AmN<CNPs-Ac<CNPs-Cl≈CNPs-N. It can be concluded that the presence of ammonium n sulfate anion significantly affects the dispersion stability of CNPs compared to that of nitrate, chloride and acetate ions. The low hydrodynamic size and high zeta potential are indication of stable suspension of CNPs particles which is beneficial due resulting increase in catalytic activity due to higher surface area and increased stability. Thus, and as shown in the data below, CNPs-Cl, CNPs-N and CNPs-Ac exhibit higher catalytic activity, indicating enhanced potential antioxidant capacities. The zeta potential values of all the CNPs do not change drastically over the duration of formation for 30 days.

Surface Chemistry of CNPs Prepared Using Different Precursor

The UV-visible spectrophotometry of Ce in CNPs provides quantitative and qualitative information about the change in oxidation states which is clearly depicted in FIG. 2A. The UV-Visible spectra of different CNPs have been recorded after 30 days. The peak around 252 nm and 290 nm corresponds to that of $Ce^{3+}$ and $Ce^{4+}$, respectively. In case of CNPs-Ac, the peak intensities of both $Ce^{3+}$ and $Ce^{4+}$ are more prominent. On the other hand, in case of CNPs-Cl, CNPs-N, CNP—AmN and CNPs-S, the peak of $Ce^{3+}$ alone is more pronounced. It has been previously reported that higher concentration of $Ce^{3+}$ on the surface is more SOD mimetic in nature [9] whereas the and higher concentration of $Ce^{4+}$ is more catalase mimetic in nature [25]. This indicates that the ratio of $Ce^{3+}/Ce^{4+}$ are more dominant in case of CNPs-Ac, CNPs-Cl and CNPs-N, indicating better SOD antioxidant mimetic activity. In case of both CNPs-AmN and CNPs-S, the $Ce^{3+}$ peak intensity is more prominent compared to $Ce^{4+}$ peak which is almost insignificant in intensity. It can also be noted that in case of CNPs-N and CNPs-Cl the $Ce^{3+}$ peak shape is more clear compared to CNPs-AmN and CNPs-S. It can be clearly inferred that even despite the same synthesis method and oxidizing agents, the change in cerium precursor salt consisting of different anion can significantly alter the surface chemistry of CNPs, generating varied potential catalytic activity.

XPS analysis of CNPs prepared using different precursors was performed on day 30 to analyze the dynamic surface chemistry of CNPs, which is mainly regulated by concentration of $Ce^{3+}$ and $Ce4^+$ on the surface. The XPS spectrum of Ce (3d) of CNPs were analyzed to calculate the $Ce^{3+}$% on the surface of the nanoparticle as shown in FIG. 2B. The results indicate that the percentage of $Ce^{3+}$ on the surface of CNPs is higher in case of CNPs-N(~55.3%) followed by CNPs-AmN (~41.1%). CNPs-Cl (~34.6%) and CNPs-S (~35%) have approximately the same amount of $Ce^{3+}$ concentration on the surface of CNPs. Furthermore, CNPs-Ac (~30.6%) has the least amount of $Ce^{3+}$ on the surface of CNPs. This indicates that the CNPs-N is inferred to have the highest SOD mimetic activity followed by CNPs-AmN, CNPs-Cl, CNPs-S and CNPs-Ac. However, the dispersion instability observed in CNPs-AmN and CNPs-S can alter the SOD mimetic activity due to scattering effects during the reading of the assay plate in UV-Visible spectroscopy. The surface chemistry analysis of different CNPs shows that the change in anion of the cerium precursor can extensively change the surface chemistry of CNPs. thereby, by using the same synthesis method, we have observed a huge difference in the surface chemistry that can lead to different antioxidant capacities of CNPs synthesized from different precursor salts.

SOD Mimetic Activity of CNPs Prepared Using Different Precursor

The superoxide dismutase activity was measured using a superoxide dismutase assay kit which uses a water-soluble tetrazolium salt, WST-1 that produces a formazan dye on reduction initiated by the superoxide anion. Pure water is used as the control to compare against the CNPs samples. The WST-1 formazan dye has an absorbance at 440 nm that can be measured using UV-Visible spectrometer. In this study, the SOD mimetic activity of CNPs was evaluated using the kit after day 30, and the % of SOD-antioxidant capacity was calculated for different CNPs prepared using different precursors. The SOD mimetic activity of different CNPs are presented in FIG. 3A, which indicates the higher SOD mimetic activity of CNPs-Cl, CNPs-N followed by CNPs-Ac. The curve farther from the negative control is more SOD mimetic active. The CNPs-S and CNPs-AmN do not depict high SOD mimetic activity which is attributed to their dispersion stability studied using DLS and surface chemistry derived from XPS analysis. The study uses UV-Visible spectroscopy measurements and due to increased scattering phenomenon of the precipitated CNPs-S and CNPs-AmN samples, due to unstable dispersion stability gives rise to erratic results. CNPs-N has the highest $Ce^{3+}$ concentration on its surface and it clearly correlated to the highest SOD mimetic activity. The equivalent SOD mimetic activity of CNPs-Cl compared to CNPs-N exhibits high SOD mimetic activity.

Figure 3B:
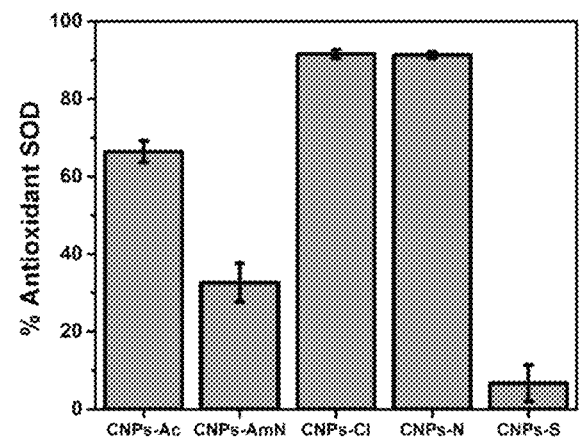

An unexpected result was that CNPs-Cl with low $Ce^{3+}$ compared to $Ce^{4+}$ exhibited high SOD mimetic activity. It can be inferred that the presence of $Cl^-$ ion is altering the catalytic antioxidant property CNPs-Cl even though these CNPs have less concentration of $Ce^{3+}$ on the surface. In-situ UV-Visible spectro-electrochemical analysis was performed to further understand the role of $Cl-$ vs $NO_3^-$ on the surface chemistry of CNPs. FIG. 3B represents the % of antioxidant capacity of CNPs calculated at 30 min of the assay time. The results of % antioxidant capacities of CNPs clearly correlate to that of the SOD mimetic activity represented in FIG. 3A. FIG. 3A indicates that CNPs-N and CNPs-Cl has the highest SOD mimetic activity followed by that of CNPs-Ac. The CNPs-S and CNPs-AmN do not depict high SOD mimetic activity which is attributed to their dispersion stability. FIG. 3 (B) shows that additionally, the rates of reaction of CNPs derived from different precursor in depicting SOD mimetic activity have been analyzed using the SOD mimetic kinetic curves. The SOD mimetic reactions were carried out of different concentration of CNPs such as 0.1 mM, 0.5 mM, 1 mM and 5 mM. It can be clearly observed that the rate of reactions of SOD mimetic activity of CNPs-Cl, CNPs-N followed by CNPs-Ac, are higher than that of CNPs-S and CNPs-AmN which correlates to the dispersion stability and surface chemistry. (B) The % of antioxidant capacity of CNPs also correlates with the above data Additionally, the rates of reaction of CNPs derived from different precursor in depicting SOD mimetic activity have been analyzed using the SOD mimetic kinetic curves as depicted in FIG. 3C. The SOD mimetic assay was carried out on different concentration of CNPs; 0.1 mM, 0.5 mM, 1 mM and 5 mM. It can be observed that the rate of scavenging of superoxide radical by CNPs increases with increase in concentration of CNPs. It can be clearly observed that the rate of reactions of SOD mimetic activity of CNPs-Cl, CNPs-N is highest followed by CNPs-Ac. The rate of scavenging of CNPs-S and CNPs-AmN, are the lowest which correlates to the dispersion stability and surface chemistry. The rate have been calculated by assuming that at a particular given time, the amount of superoxide radicals consumed by the CNPs is proportional to the difference of superoxide radicals consumed by WST-1 reagent competes with CNPs and when WST-1 competes with water (control). The change in rate with increase in concentration provides an in depth understanding of CNPs in terms of enzymatic kinetics. This can be correlated to Michaelis-Menten saturation curves for an enzyme reaction showing the relation between the substrate concentration and reaction rate.

Figure 4:
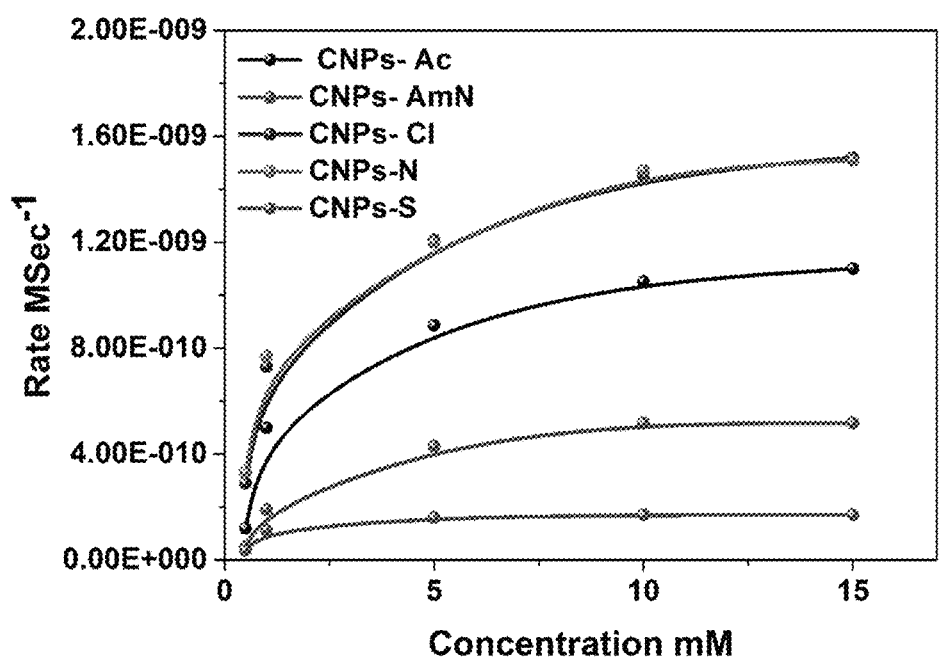
FIG. 4 shows the Michaelis-Menten kinetics of CNPs prepared using different precursors.

Quantification of Enzymatic Mimetic Activity of CNPs Prepared Using Different Precursor The rates of reaction of CNPs (CNPs-Ac, CNPs-AmN, CNPs-Cl, CNPs-N, and CNPs-S) that are pertinent to their SOD mimetic activities have been analyzed employing the SOD mimetic kinetics (see FIG. 4). The SOD-mimetic assays have been performed using different concentrations of hypoxanthine (which produces $O_2^{\bullet-}$ upon reaction with xanthine oxidase, the substrate that binds to the enzyme CNPs in the enzymatic reaction adopted for analyzing enzymatic kinetics): 0.1, 0.5, 1, and 1.5 mM. From FIG. 4 it can be observed that the rates of scavenging of $O_2^{\bullet-}$ by $$v = \frac{d[P]}{dt} = \frac{V_{max} + [S]}{K_M + [S]}$$

Here, $V_{max}$ represents the maximum rate achieved by the enzymatic reaction, at the maximum saturating substrate concentrations. The Michaelis constant given by $K_M$ which is the substrate concentration at which the reaction rate is half of $V_{max}$. Using nonlinear regression of the Michaelis-Menten equation and using the plot of reaction rate against concentration, the values of $K_M$ and $V_{max}$ have been calculated. The rate of reaction ($O_2^{\bullet-}$ scavenging) increases with increase in the concentration of substrate, approaching the $V_{max}$ when all of the $O_2^{\bullet-}$ radical is consumed by CNPs. A higher value of $K_M$ indicates higher affinity, which means that the value of $V_{max}$ is quickly being approached.

The calculated enzyme-like kinetics of CNPs (see FIG. 4 and Table 1) have been found to be comparable to that of SOD enzymes (19). The second-order rate constants of SOD enzymes are calculated to be of the order of 109 M-1 sec-1 depending on the kind of SOD enzyme and the pH of the solution (19). Therefore, these values are comparable to the Vmax (reaction rates) values of CNPs-Cl, CNPs-N, and CNPs-Ac (see Table 1).:

TABLE 1

| SAMPLE | Ac | AmN | Cl | N | S |
| --- | --- | --- | --- | --- | --- |
| Vmax (M/sec^-1) | 1.093E-09 | 5.11E-10 | 1.512E-09 | 1.5302E-09 | 1.72E-10 |
| Km (mM) | 0.188 | 0.25 | 0.161 | 0.159 | 0.46 |

CNPs increase with rise in concentration of hypoxanthine. Furthermore, the data in FIG. 4 show that the rates of reactions involved in the SOD-mimetic activities of CNPs-Cl and CNPs-N are the highest followed by that of CNPs-Ac. The rate of $O_2^{\bullet-}$ scavenging of CNPs-S and CNPs-AmN are found to be the lowest; these results correlate well to the dispersion stability of these CNPs. The rates have been calculated by assuming that at a particular given time, the amount of $O_2^{\bullet-}$ scavenged by CNPs is proportional to the difference between the extent of $O_2^{\bullet-}$ scavenged by WST-1 reagent in the presence of CNPs and that in the absence of CNPs (i.e., water control). The change in the rate of $O_2^{\bullet-}$ scavenging with increase in substrate concentration provides an in-depth understanding of CNPs in terms of enzymatic kinetics. This can be correlated to the Michaelis-Menten saturation curve for an enzyme reaction that shows the relation between the substrate concentration and reaction rate. The Michaelis-Menten kinetics data are presented in FIG. 4. It is clearly evident from FIG. 4 that the rates of $O_2^{\bullet-}$ scavenging by CNPs-N and CNPs-Cl are found to be higher than that by CNPs-Ac, whereas the corresponding rates of $O_2^{\bullet-}$ scavenging by CNPs-S and CNPs-AmN are found to be lower. These results correlate well to those already reported in FIGS. 1-3 for the physiochemical studies of CNPs that include investigations of hydrodynamic size, zeta potential, UV-visible spectra results, XPS analysis, and of SOD-mimetic activity.

Michaelis-Menten kinetics is one of the best-known models to quantify enzymatic kinetics in biochemistry. The model correlates the rate of the enzymatic reaction (v), with the concentration of a substrate [S] given by the formula below:

Michealis-Menten constants Vmax and Km have been calculated from the Michaelis-Menten fitted curves. Table 1 presents the Michaelis-Menten constants derived from the fitted curves in FIG. 4.

Effect of Cl⁻ and $NO_3^-$ on the Enzymatic Catalytic Properties of CNPs

The effect of Cl⁻ and $NO_3^-$ on the catalytic activity of CNPs was confirmed by using SOD assay kit and UV-Visible spectro-electrochemistry analysis. These investigation enabled the elucidation of the reason behind unusual higher SOD mimetic activity of CNPs-Cl with low concentration of $Ce^{3+}$. The concentration of the counter ions Cl⁻ and $NO_3^-$ were varied by adding NaCl and $NaNO_3$ salts at different concentration to see the effect of the individual ions on the respective CNPs-Cl and CNPs-N. The SOD assay of the respective CNPs made with different ceria salts and the added NaCl, $NaNO_3$ salts along with CNPs-N, CNPs-Cl have been analyzed. This is to confirm that the added NaCl and $NaNO_3$ salts are not SOD mimetic active by themselves compared to CNPs-Cl and CNPs-N.

FIG. 5A presents the expected results showing that $CeNO_3$ has SOD mimetic activity due to the presence of Ce3+ ions in the system. $NaNO_3$ does not exhibit SOD mimetic activity as $NO_3^-$ and Na+ ions by themselves are not SOD active and CNPs-N is SOD mimetic active as mentioned previously. In FIG. 5B, it is shown that $CeCl_3$, exhibits SOD mimetic activity due to the presence of Ce3+ ions in the system, NaCl does not exhibit SOD mimetic activity as Cl- and Na+ ions by themselves are not SOD mimetic active and CNPs-Cl is SOD mimetic active as previously mentioned.

Furthermore, the SOD mimetic activity was tested with different concentrations of NO3- and Cl- ions. This can provide an in-depth understanding into whether the anions have an effect on the SOD antioxidant properties of CNPs even though they do not possess any SOD mimetic activity of their own. The SOD mimetic assay was performed on CNPs-N and CNPs-Cl samples with different concentrations of NO3– and Cl– ions respectively. FIG. 6A shows that the SOD mimetic activity of different CNP—N samples with varied concentrations of 0.03 mM, 0.3 mM, 3 mM and 30 mM of NO3– did not have much effect on the SOD mimetic activity. Whereas in FIG. 6B, the increasing addition of Cl– clearly effected the SOD mimetic activity of CNP-Cl. It can be inferred that the presence of Cl– is effecting the SOD mimetic activity of CNPs. The effect of Cl– is comparatively more than that of NO3– on the SOD mimetic activity of CNPs as depicted in FIG. 6C.

To further understand how the Cl– and NO3– ion is affecting the SOD mimetic activity of CNPs, UV-Visible spectro-electrochemistry was performed to gauge if the oxidation potentials of CNPs are affected in the presence of the ions. Open circuit potentials (OCP) values were recorded of CNPs-N with increasing concentration of $NO^-_3$ ions and CNPs-Cl with increasing concentrations of $Cl^-$ ions. The ions concentrations were varied form 0, 0.3 mM, 3 mM and 30 mM.

FIG. 7A shows that the OCP of CNPs-N increases with increase in concentration of $NO^-_3$ ions whereas the OCP of CNPs-Cl decreases with increase in concentration of $Cl^-$. The oxidation potential is the ability of the entity to oxidize other species. In case of CNPs is the oxidation potential is more, it gets harder to oxidize itself, thereby the ability to convert $Ce^{4+}$ to $Ce^{3+}$ decreases. This indicates that with the increase in CF ions the oxidation potential of CNPs ($Ce^{3+}$ converting to $Ce^{4+}$) decreases, indicating the increase in ability to convert $Ce^{4+}$ to $Ce^{3+}$ on the surface of CNPs-Cl. On the other hand, with the increase in $NO^-_3$ ions the activity and oxidation potential of CNPs-N decreases, showing the decrease in ability to convert $Ce^{4+}$ to $Ce^{3+}$. This shows a drastic effect of two different ions on the oxidation potentials of CNPs.

Furthermore, UV-Visible spectroscopy have been recorded at application of different voltages of 0V, 0.1V, 0.5V, 0.7V, 0.8V to the CNPs-N samples as shown in FIG. 7B showing an increase in change of the intensity of $Ce^{3+}$ peak with increase in voltage. On the other hand in the case of CNPs-N with the addition of 30 mM $NO^-_3$ ions (FIG. 7C) exhibits a decrease in the ability of the increase in the intensity of $Ce^{3+}$ peak, which is not as strong when there were no added $NO^-_3$ ions in the system (FIG. 7B). This indicates that there is an oxidation of $Ce^{3+}$ with the increase in voltage of the CNPs-N peak and this intensity of increase is altered by the change in concentration of added $NO^-_3$ ions. In case of CNPs-Cl, the UV-Visible graph of $Ce^{3+}$ peak of CNPs-Cl after applying varying voltages of 0V, 0.1V, 0.5V, 0.8V, 1V, 1.2V, 1.5V depicted in FIG. 7D indicated no change in the intensity of $Ce^{3+}$ peak with increase in voltage. This indicates that there was no oxidation of $Ce^{3+}$ with the increase in voltage in CNPs-Cl, whereas there was a clear increase in intensity of $Ce^{3+}$ of CNPs-N. This reestablishes the fact there is a clear change in the way surface chemistry changes with the application of voltage in presence of two different ions in CNPs. In FIG. 7E, the UV-Visible graph of $Ce^{3+}$ peak of CNPs-Cl with the addition of 30 mM CF ions after applying varying voltages changes intensity has been presented. This indicates that there is an oxidation of $Ce^{3+}$ with the increase in voltage of the CNPs-Cl in presence of additional Cl– ions. This additionally indicates that with the increase in concentration of Cl– ions, the change in surface chemistry of CNPs-Cl is highly affected when voltage is applied to the CNPs-Cl solutions. Therefore, it can be clearly observed that $Cl^-$ indeed effects the oxidation of $Ce^{3+}$ to $Ce^{4+}$ in CNPs. This affects the fact that even though CNPs-Cl has more 4+ it is an SOD mimetic likely due to altered potentials of $Ce^{3+}$ to $Ce^{4+}$ transition in presence of CF ions.

ESR Studies

ESR studies have been carried out to test whether the anion (e.g., NO3-) from the precursor salt (e.g., cerium nitrate) is still present at the surface of the CNPs synthesized. CNPs-N and CNPs-Cl, which have been synthesized from two precursors, cerium(III) nitrate and cerium(III) chloride, have been chosen for ESR studies. Concentration and size of CNPs used for the ESR studies have been found to be identical (5 mM, 3-5 nm). On the basis of the findings that the DNA radicals in glassy systems (7.5 M LiBr) at low temperature undergo reactions that are similar in aqueous solutions at ambient temperatures, (21, 26) it is believed that CNPs should show similar surface chemistry upon rapid cooling of the aqueous solutions to liquid N2 temperature (77 K) in glassy systems. Results of the ESR studies are shown in FIGS. 9A-9B.

The 2 min UV-photoionization of the 5'-dGMP sample (2 mg/mL) at 254 nm and at 77 K in 7.5 M LiCl/H2O and in the presence of 2.5 mM CNPs that have been synthesized from the precursor salt cerium(III) nitrate has resulted in the blue spectrum shown in FIG. 8A. To verify that the blue spectrum showed line components owing to NO3•2–, a glassy sample (7 M LiBr/D2O) of NaNO3 (1 mg/mL) was γ-irradiated (absorbed dose=500 Gy) at 77 K, and subsequently its ESR spectrum was recorded at 77 K. This spectrum (pink) is shown in FIG. 9A. Instead of H₂O glass, the D2O glass was used because it improves the spectral resolution by narrowing the line-widths. Because NO3– is a well-known scavenger of radiation-produced electrons forming NO3•2–, the green spectrum is assigned to NO3•2– in a glassy system at 77 K. The radiation-produced holes led to the formation of Br2.–, and this has been found to be ESR-mute in the spectral region (250 G). (42)

Figures 9A, 9B:
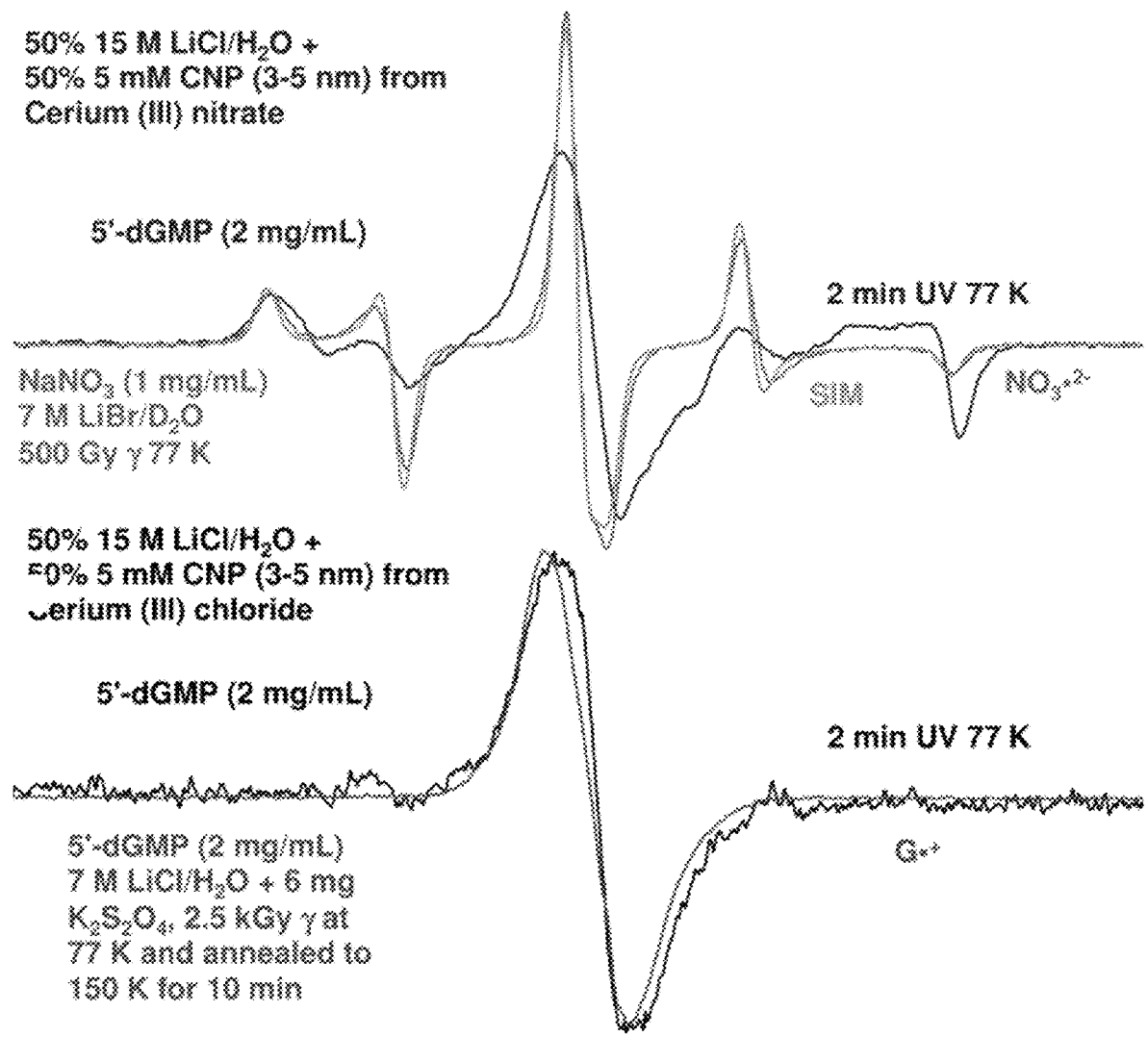
FIG. 9A-B.

Superimposition of the pink spectrum due to NO3•2– with that of the blue spectrum in FIG. 9A clearly showed that the blue spectrum exhibited line components owing to $NO_3^{•2-}$. This result proved that the CNPs synthesized from cerium nitrate as precursor still contained the anion ($NO_3$—) from the precursor salt. Comparison of panels A and B of FIG. 9 shows that apart from the line component due to $NO_3^{•2-}$, the center of the blue spectrum in FIG. 9A also has line components owing to guanine cation radical, G•+ (see eq 1 and discussion of FIG. 9B, vide infra).

It is noted here that the pink spectrum due to $NO_3^{•2-}$ in FIG. 9A has been simulated (green spectrum in FIG. 9A) employing the ESR parameters A(N)=(65.8, 33.5, 33.5) G, (gxx, gyy, gzz)=(2.001, 2.0055, 2.0055), and with a mixed (Lorentzian/Gaussian=0.4) line width=4 G. Superimposition of the green spectrum on the experimentally recorded pink spectrum due to $NO_3^{•2-}$ showed the nice agreement between these two spectra. It is also noted here that isotropic N hyperfine coupling constant (HFCC) value (44.3 G) for N in $NO_3^{•2-}$ in the glassy system at 77 K is found to be in excellent agreement with those reported earlier for N in $NO_3^{•2-}$ in single crystals (A(N)=(61, 32, 32) G, (gxx, gyy, gzz)=(2.002, 2.006, 2.006)); these earlier isotropic N HFCC value (41.7 G) corresponded to a ca. 13° deviation from planarity. (27) The nice match between the simulated spectrum (green) and the experimentally recorded spectrum (pink) of $NO_3^{•2-}$ spectrum confirms our assignments of line components due to $NO_3^{•2-}$ spectrum in the blue spectrum in FIG. 9A. The expected line broadening from D₂O to H₂O (compare pink spectrum with blue spectrum in FIG. 9A) is indeed observed owing to larger dipolar interactions in H$_2$O.

The 2 min UV-photoionization of the 5'-dGMP sample (2 mg/mL) at 254 nm and at 77 K in 7.5 M LiCl/H$_2$O and in the presence of 2.5 mM CNPs-Cl which has been synthesized from the precursor salt cerium(III) chloride, has resulted in the black spectrum shown in FIG. 9B. Comparison of the black spectrum in FIG. 9B with the blue spectrum in FIG. 9A evidences the presence of prominent line components of NO$_3^{\bullet 2-}$ in the blue spectrum. The red spectrum, following our works on generation of G$^{\bullet+}$ via one-electron oxidation by Cl2•− in the homogeneous supercooled glassy (7.5 M LiCl either in D$_2$O or in H$_2$O) solutions of DNA- and RNA-models containing guanine, is generated. (22-25, 31) The one-electron oxidation of 5'-dGMP by Cl$_2^{\bullet-}$ has been carried out via thermal annealing at 150 K for 10 min in the dark. The red spectrum has been assigned to G$^{\bullet+}$. Comparison of this red spectrum due to G$^{\bullet+}$ with the black spectrum in FIG. 9B as well as with the blue spectrum in FIG. 8A evidences the formation of G$^{\bullet+}$ via photoionization of 5'-dGMP in the presence of CNPs in the glassy system (see eq 1). This is the first report showing formation of G$^{\bullet+}$ via photoionization of 5'-dGMP in the presence of CNPs in the glassy system. ESR studies on CNPs synthesized from cerium(III) nitrate showed the evidence of nitrate anion radical (NO$_3^{\bullet 2-}$) formation due to radiation-produced prehydrated electron capture by NO$_3^-$ (see eq 2).

$$G \rightarrow G^{\bullet+} + e^- \quad (1)$$

$$NO_3^- + e^- \rightarrow NO_3^{\bullet 2-} \quad (2)$$

This result has established the presence of the anion (i.e., NO$_3^-$) in the surface of CNPs synthesized from cerium(III) nitrate. Radiation chemical studies on the reactivities of electrons have established that Cl$^-$ is not a scavenger of radiation-generated electrons while NO$_3^-$ is a very effective electron scavenger. (27) Thus, our ESR work establishes that Cl$^-$ on the surface of CNPs-Cl does not contribute to the scavenging of radiation-produced electrons. Consequently, our ESR results point out that Ce4+ in the surface of the CNPs-Cl appears to be a better scavenger of radiation-produced electrons by reaction with Ce4+ generating more Ce3+(see eq 3) on its surface than that for CNPs-N. This is because, in the case of CNPs-N, the radiation-produced electrons are predominantly scavenged by NO$_3^-$.

$$Ce^{4+} + e^- \rightarrow Ce^{3+} \quad (3)$$

CONCLUSIONS

The above examples represent efforts to explore whether a significant change in surface chemistry of CNPs can be achieved by changing the anion on the precursor cerium salt, despite using the same method of preparation. In this work, the extensive physiochemical investigations of CNPs (CNPs-Ac, CNPs-AmN, CNPs-Cl, CNPs-N, and CNPs-S) have shown that CNPs-S and CNPs-AmN have lower zeta potentials and higher hydrodynamic sizes. These results have established that the hexanitratocerate ([(Ce(NO$_3$)$_6$)]$^{2-}$) and sulfate ions (SO$_4^{2-}$) alter the dispersion stability of CNPs in aqueous solutions. Our results have established that the dispersion stabilities of CNPs follow the descending order CNPs-S<CNPs-AmN<CNPs-Ac<CNPs-Cl≈CNPs-N. Additionally, the surface chemistry studied using UV-visible spectroscopy and XPS has been observed to be affected significantly by the presence of the anions from the precursor salt in CNPs. Furthermore, our results show that the percentage of Ce3+ on the surface of CNPs is higher in the case of CNPs-N followed by that of CNPs-AmN. The SOD-mimetic activity and the rates of removal of superoxide anion radical have been found to be highest for CNPs-N and CNPs-Cl followed by those for CNPs-Ac. The fact that CNPs-S and CNPs-AmN have not exhibited high SOD-mimetic activity can be attributed to their decreased dispersion stability. One of the most interesting findings in this particular study is the unusual higher SOD-mimetic activity of CNPs-Cl in spite of the low concentration of Ce3+ on its surface. In this study, the effects of Cl− and NO3− ions on CNPs have been investigated further by employing the SOD-mimetic analysis and UV-visible spectro-electrochemistry of CNPs-Cl and CNPs-N with varying concentrations of the respective chloride and nitrate anions. The work with CNPs-Cl shows that the presence of Cl− alters the SOD mimetic activity, indirectly altering the surface chemistry. The OCP characterization has revealed that the increase in concentration of Cl− ions decreases the oxidation potential of CNPs, whereas raising the concentration of NO3− ions in the CNPs-N solution increases the oxidation potential of CNPs-N. Most importantly, ESR studies clearly show the presence of surface counter ions (e.g., NO3− in CNPs-N) even in the presence of 7 M LiBr. This indicates a major breakthrough in recognizing the role of ions on the surface chemistry, oxidation potential, and antioxidant properties of CNPs. Thus, the foregoing work demonstrates the fact that even though the same synthesis method and oxidizers are used, just the change in the anion of the precursor salt can extensively change the physiochemical properties of nanoparticles.

CNPs-N and CNPs-Cl were chosen for ESR studies and the ESR results are presented in FIGS. 9A-9B. A 5'-dGMP sample (2 mg/mL) in 7.5 M LiCl/H$_2$O and in the presence of 2.5 mM CNP—N was UV-photoionized at 254 nm for 2 min at 77 K. The blue ESR spectrum due to this photoionization is shown in FIG. 9A. The line components due to NO$_3^{\bullet 2-}$ are present in the blue spectrum and this is verified by recording a 77 K ESR spectrum (pink, FIG. 9A) of a glassy sample (7 M LiBr/D$_2$O) of NaNO$_3$ (1 mg/mL) that was γ-irradiated (absorbed dose=500 Gy, 77 K) and by a simulated spectrum (pink, FIG. 9A) due to NO$_3^{\bullet 2-}$. The ESR parameters (hyperfine coupling constants and g-values) used for simulation agreed nicely with the reported ones in the literature. A matched 5'-dGMP sample (2 mg/mL) in 7.5 M LiCl/H$_2$O and in the presence of 2.5 mM CNP-Cl was UV-photoionized at 254 nm for 2 min at 77 K. The black ESR spectrum due to this photoionization is shown in FIG. 9(B) and is assigned to guanine cation radical (G$^{\bullet+}$) are on the basis of reported G$^{\bullet+}$ spectrum in the literature. As Cl$^-$ is a poor scavenger of radiation-produced electrons, Cl$^{\bullet 2-}$ is never produced and is not observed by ESR. This the first report of guanyl radical ESR spectrum in presence of CNPs.

The above description is provided as an aid in examining particular aspects of the invention, and represents only certain embodiments and explanations of embodiments. The examples are in no way meant to be limiting of the invention scope. The materials and methods provided include those which were used in performing the examples above.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

REFERENCES

1. Lohse, S. E. and C. J. Murphy, *Applications of colloidal inorganic nanoparticles: from medicine to energy*. Journal of the American Chemical Society, 2012. 134(38): p. 15607-15620.
2. Das, S., et al., *Cerium oxide nanoparticles: applications and prospects in nanomedicine*. Nanomedicine, 2013. 8(9): p. 1483-1508.
3. Yang, J. C., H.-j. Kim, and T. Kim, *Study of polishing characteristics of monodisperse ceria abrasive in chemical mechanical planarization*. Journal of The Electrochemical Society, 2010. 157(3): p. H235-H240.
4. Rodriguez, J. A., et al., *Water☐Gas Shift Reaction on a Highly Active Inverse CeOx/Cu (111) Catalyst: Unique Role of Ceria Nanoparticles*. Angewandte Chemie, 2009. 121(43): p. 8191-8194.
5. Masui, T., et al., *Synthesis of BN-coated CeO2 fine powder as a new UV blocking material*. Journal of Materials Chemistry, 2000. 10(2): p. 353-357.
6. Eguchi, K., et al., *Electrical properties of ceria-based oxides and their application to solid oxide fuel cells*. Solid State Ionics, 1992. 52(1-3): p. 165-172.
7. Karakoti, A. S., et al., *Preparation and characterization challenges to understanding environmental and biological impacts of ceria nanoparticles*. Surface and Interface Analysis, 2012. 44(8): p. 882-889.
8. Xu, J., et al., *Size dependent oxygen buffering capacity of ceria nanocrystals*. Chemical communications, 2010. 46(11): p. 1887-1889.
9. Heckert, E. G., et al., *The role of cerium redox state in the SOD mimetic activity of nanoceria*. Biomaterials, 2008. 29(18): p. 2705-2709.
10. Karakoti, A., et al., *Nanoceria as antioxidant: synthesis and biomedical applications*. JOM Journal of the Minerals, Metals and Materials Society, 2008. 60(3): p. 33-37.
11. Chigurupati, S., et al., *Effects of cerium oxide nanoparticles on the growth of keratinocytes, fibroblasts and vascular endothelial cells in cutaneous wound healing*. Biomaterials, 2013. 34(9): p. 2194-2201.
12. Barkam, S., et al., *The Change in Antioxidant Properties of Dextran☐Coated Redox Active Nanoparticles Due to Synergetic Photoreduction—Oxidation*. Chemistry-A European Journal, 2015. 21(36): p. 12646-12656.
13. Deshpande, S., et al., *Size dependency variation in lattice parameter and valency states in nanocrystalline cerium oxide*. Applied Physics Letters, 2005. 87(13): p. 133113.
14. Sun, C., H. Li, and L. Chen, *Nanostructured ceria-based materials: synthesis, properties, and applications*. Energy & Environmental Science, 2012. 5(9): p. 8475-8505.
15. Dowding, J. M., et al., *Cellular interaction and toxicity depend on physicochemical properties and surface modification of redox-active nanomaterials*. ACS nano, 2013. 7(6): p. 4855-4868.
16. Zhang, F., Q. Jin, and S.-W. Chan, *Ceria nanoparticles: size, size distribution, and shape*. Journal of applied physics, 2004. 95(8): p. 4319-4326.
17. Lynch, I. and K. A. Dawson, *Protein-nanoparticle interactions*. Nano today, 2008. 3(1): p. 40-47.
18. Das, S., et al., *The induction of angiogenesis by cerium oxide nanoparticles through the modulation of oxygen in intracellular environments*. Biomaterials, 2012. 33(31): p. 7746-7755.
19. Korsvik, C., et al., *Superoxide dismutase mimetic properties exhibited by vacancy engineered ceria nanoparticles*. Chemical Communications, 2007(10): p. 1056-1058.
20. Celardo, I., et al., *Ce3+ ions determine redox-dependent anti-apoptotic effect of cerium oxide nanoparticles*. Acs Nano, 2011. 5(6): p. 4537-4549.

21. Kumar, A., et al., *Luminescence properties of europium-doped cerium oxide nanoparticles: role of vacancy and oxidation states*. Langmuir, 2009. 25(18): p. 10998-11007.
22. Hirst, S. M., et al., *Anti☐inflammatory Properties of Cerium Oxide Nanoparticles*. Small, 2009. 5(24): p. 2848-2856.
23. Langergraber, G., N. Fleischmann, and F. Hofstaedter, *A multivariate calibration procedure for UV/VIS spectrometric quantification of organic matter and nitrate in wastewater*. Water science and technology, 2003. 47(2): p. 63-71.
24. Freitas, C. and R. H. Müller, *Effect of light and temperature on zeta potential and physical stability in solid lipid nanoparticle (SLN™) dispersions*. International journal of pharmaceutics, 1998. 168(2): p. 221-229.
25. Pirmohamed, T., et al., *Nanoceria exhibit redox state-dependent catalase mimetic activity*. Chemical communications, 2010. 46(16): p. 2736-2738.
26. Adhikary, A.; Kumar, A.; Becker, D.; Sevilla, M. D. The Guanine Cation Radical: Investigation of Deprotonation States by ESR and DFT. J. Phys. Chem. B 2006, 110, 24171-24180.
27. Atkins, P. W.; Symons, M. The structure of inorganic radicals; Elsevier Publishing Company: Amsterdam, 1967.

What is claimed is:

1. A composition comprising cerium nanoparticles (CNPs) in the presence of chloride ions, the CNPs formed from a reduction of a cerium precursor salt having a chloride anion, and wherein the CNPs have a predominant 4+ surface charge and exhibit SOD mimetic activity, and wherein the CNPs are of a size range of 1 nm to 20 nm and comprise a zeta-potential of more than 30 mV.

2. A composition of claim 1, wherein the concentration of the chloride ions is at least 0.03 mM.

3. The composition of claim 1, wherein the chloride ions are produced by the reduction of the cerium precursor salt having a chloride anion.

4. The composition of claim 1, wherein the composition comprises additional chloride ions in addition to any chloride ions produced by the reduction of the cerium precursor salt.

5. The composition of claim 4, wherein the additional chloride ions are provided by adding sodium chloride.

* * * * *